United States Patent [19]

Matschke et al.

[11] Patent Number: 4,764,473
[45] Date of Patent: Aug. 16, 1988

[54] CHAMBER FOR THE TREATMENT OF CELLS IN AN ELECTRICAL FIELD

[75] Inventors: Christain Matschke, Alsdorf; William M. Arnold; Karl-Heinz Büchner, both of Jülich; Ulrich Zimmerman, Hürtgenwald-Gey, all of Fed. Rep. of Germany

[73] Assignee: Kerforshungsanlage Julich, Fed. Rep. of Germany

[21] Appl. No.: 926,861

[22] Filed: Nov. 4, 1986

Related U.S. Application Data

[63] Continuation of Ser. No. 609,274, May 11, 1984, abandoned.

[30] Foreign Application Priority Data

May 13, 1983 [DE] Fed. Rep. of Germany ....... 3317415

[51] Int. Cl.⁴ .................. C12M 1/00; C12M 1/24; C12M 1/02; C12N 13/00
[52] U.S. Cl. .................... 435/287; 435/173; 435/296; 435/316; 204/272; 204/275; 204/241; 204/131
[58] Field of Search .............. 435/173, 287, 296, 316, 435/292, 293, 294, 172.2, 299, 300; 935/93; 128/783, 789; 204/272, 275, 241, 131

[56] References Cited

U.S. PATENT DOCUMENTS

| | | | |
|---|---|---|---|
| 2,588,223 | 3/1952 | Erickson | 435/173 X |
| 2,830,945 | 4/1958 | Keidel | 204/430 |
| 3,081,250 | 3/1963 | Hall et al. | 204/430 |
| 3,095,359 | 6/1963 | Heller | 435/173 X |
| 3,875,012 | 4/1975 | Dorn et al. | 435/296 X |
| 4,210,418 | 7/1980 | Brown et al. | 435/296 X |
| 4,561,961 | 12/1985 | Hofmann | 204/302 X |
| 4,578,168 | 3/1986 | Hofmann | 204/302 X |
| 4,622,302 | 11/1986 | Sowers | 435/173 |
| 4,695,547 | 9/1987 | Hilliard et al. | 204/272 X |
| 4,699,881 | 10/1987 | Matschke | 204/272 X |

FOREIGN PATENT DOCUMENTS

3317415 11/1984 Fed. Rep. of Germany ........ 935/93

OTHER PUBLICATIONS

Zimmerman et al., J. Membrane Biol. vol. 67, 1982, pp. 165–182.
Zimmerman et al., Biotechniques, Sep./Oct. 1983, pp. 118–122.
Zimmerman et al., J. Biol. Phys., vol. 10, 1982, pp. 43–50.
Zimmerman et al., Biochimica at Biophysica Acta, vol. 694, 1982, pp. 227–277.
Crane, American Biotechnology Laboratory, vol. 1, 1983, pp. 74–79.

*Primary Examiner*—Robert J. Warden
*Assistant Examiner*—Randall E. Deck
*Attorney, Agent, or Firm*—Lorusso & Loud

[57] ABSTRACT

A chamber for the treatment of cells in an electrical field, in which a space is provided to hold the suspension containing the cells and into which extend at least two electrodes. The cells are exposed to an electrical field developed between the electrodes. The chamber is also provided with an accessory vessel removably connected thereto for further treatment of the cells.

14 Claims, 5 Drawing Sheets

CHAMBER FOR THE TREATMENT OF CELLS IN AN ELECTRICAL FIELD

BACKGROUND OF THE INVENTION

This invention concerns a chamber for the treatment of cells in an electrical field, in which a space formed from electrically nonconducting walls is provided to hold the suspension containing the cells, into which extend at least two electrodes in such a way that a region bounded by them is formed between the electrodes, the cells being exposed to an electrical field developed between the electrodes.

A process is known from German Pat. No. 24 05 119 for the treatment of cells in an electrical field, in which the membrane of cells is pierced by applying an electrical field whose strength is $10^3$ to $10^5$ V/cm. The increase of permeability of the cell membrane thus produced makes it possible to interchange substances through the membrane without impairing the viability of the cells, since the increase of the permeability is reversible in a simple procedural step after the interchange of the substances. It is also possible in this way, for example, to incorporate genes or enzymes into the cells.

The process for increasing the permeability of the cell membrane disclosed by the aforementioned Patent can also be used for the fusion of cells.

Two cells in a suspension, if they touch one another and if there is a close contact between the membranes of the two cells, should fuse with one another, since the fundamental units in the membrane are mobile. However, such a spontaneous fusion of cells is extremely seldom, or never, observed under natural conditions. The fertilization of an egg cell by a sperm cell in sexual propagation represents a known exception. The spontaneous fusion is prevented by the negative charge of the phospholipids and other membrane components. It leads to the repulsion of the cells when they have approached to within a small distance of one another. However, cell fusion requires the two membranes to be able to approach one another to a distance of less than $10^{-7}$ cm.

The fusion of cells carried out by technical means, or synthetically, can be used for a broad range of applications. Thus, it is of great interest for biological-medical research to fuse a large number of cells with one another. With a suitable size of the large cells formed by the fusion of several or optionally many cells—for example, 1,000 to 10,000 blood corpuscles—microelectrodes, micro pressure-measurement probes, and other sensors can then be introduced into the large cell without irreversible destruction of the membrane. The technique of measuring directly a number of cell and membrane functions through the sensors is important for clinical diagnoses, for example in the early recognition of illnesses and generally for basic research.

The technique of fusion of cells can also be used for the formation of hybrid cells by the fusion of two cells of different origin, which should not be too far removed from one another in evolution. Cell hybrids can thus be formed from plant cells, from which whole plants can again be grown, or cell hybrids from animal cells through which the monoclonal antibodies can be obtained, such as those against tumors and leukemia. An example which can be mentioned is the fusion of a lymphocyte cell with a myeloma cell, which is of great interest in particular from the medical and pharmaceutical viewpoints. Certain lymphocytes form antibodies against foreign substances in the organism, for example against a foreign protein which has been injected into the bloodstream. If the lymphocytes are isolated and fused with a tumor cell such as a myeloma cell, there is a chance that a so-called hybridoma cell will be formed, which has the nature of both parent cells. This cell produces antibodies, specifically only against the foreign substance involved (so-called monoclonal antibodies). It is immortal, and in contrast to a normal differentiated cell such as a lymphocyte, can be propagated permanently in nutrient media.

A process for the fusion of cells of the type mentioned initially is known from Biochimica et Biophysica Acta, 694 (1982), 227–277 (Electric Field-Mediated Fusion and Related Electrical Phenomena, U. Zimmermann). In this known procedure, the progress of which can be observed under the microscope, the membrane contact is produced between at least two cells by the application of an alternating, poorly homogeneous field. Because of polarization processes in the cell, dipoles are produced by the electrical field which mutually attract one another when the cells approach one another during their migration in the electrical field (so-called dielectrophoresis). After the formation of the sets of cells, the disturbances in the membrane structure between neighboring cells are triggered by an electrical breakdown pulse (J. Membrane Biol. 67, 165–182 (1982), Electric Field-Induced Cell-to-Cell Fusion, U. Zimmermann and J. Vienken). According to the models proposed up to now, holes are thus produced in the membrane contact zones of adjacent cells which lead to a cytoplasmic continuum between the two cells and to bridge formation by lipids between the membranes of adjacent cells. The lipid molecules are no longer lined up in their original membrane. As soon as such a bridge has formed, the structure formed, which consists of the cells joined together through the lipid bridges, becomes rounded off for energy reasons.

To carry out this known process, a chamber of the type described initially is used. To form the sets of cells, the electrodes of the chamber are connected to a device for producing an alternating electric field and to a device for producing electrical voltage pulses to produce the electrical breakdown.

In implementing the known process, it is endeavored, if possible, to subject all of the cells present in a suspension to the electrical treatment to increase the effectiveness of the process. This assumes that as many of the cells introduced into the chamber as possible are exposed to the electrical field. The dead zones in the chamber should therefore be as small as possible.

It is the purpose of this invention to describe a chamber of the type mentioned initially, in which a large fraction of the cells introduced into the chamber are exposed to the electrical field. The chamber is also intended to make possible the simultaneous and uniform treatment of a large number of cells.

SUMMARY OF THE INVENTION

The basic problem discussed above is solved pursuant to the invention by providing that the space for holding the suspension containing the cells is bounded laterally by an internal element and an outer cover surrounding the internal element at a constant distance from its longitudinal axis, and that the electrodes extending into the space surround the internal element in the form of a multiple screw with constant pitch, and that the region bounded by the electrodes is designed as a component region of the space in the form of a multiple screw surrounding the internal element around its longitudinal axis.

The electrodes and the bounded region, for example, are designed in the form of a double helix, a four-fold helix, etc.

A very beneficial embodiment of the chamber consists of each electrode having the same distance on both sides to the adjacent other electrode. This has the effect that the field variation is uniform between two adjacent electrodes, whereby the effective length of the electrodes is practically doubled.

The elongated internal element is appropriately cylindrical and the outer cover is designed as a cylindrical jacket with a common central axis. However, the elongated internal element can also have an oval or even a square cross section, for example, differing from the ideal circular shape, to which the internal shape of the outer cover is matched in each case.

A suitable embodiment of the chamber pursuant to the invention consists of the electrodes resting against the internal element. It is also suitable here to conduct the electrode leads through the internal element to the outside.

In another embodiment of the chamber, the electrodes rest against the inner wall of the outer cover.

Another beneficial embodiment of the chamber pursuant to the invention consists of providing an accessory vessel which can be removably connected to the outer cover, connected with the opening in the outer cover.

BRIEF DESCRIPTION OF THE DRAWINGS

Examples of the chamber pursuant to the invention are illustrated schematically in the drawing, and are described in detail below.

DETAILED DESCRIPTION OF THE PREFERRED EMBODIMENTS

Figure 1:
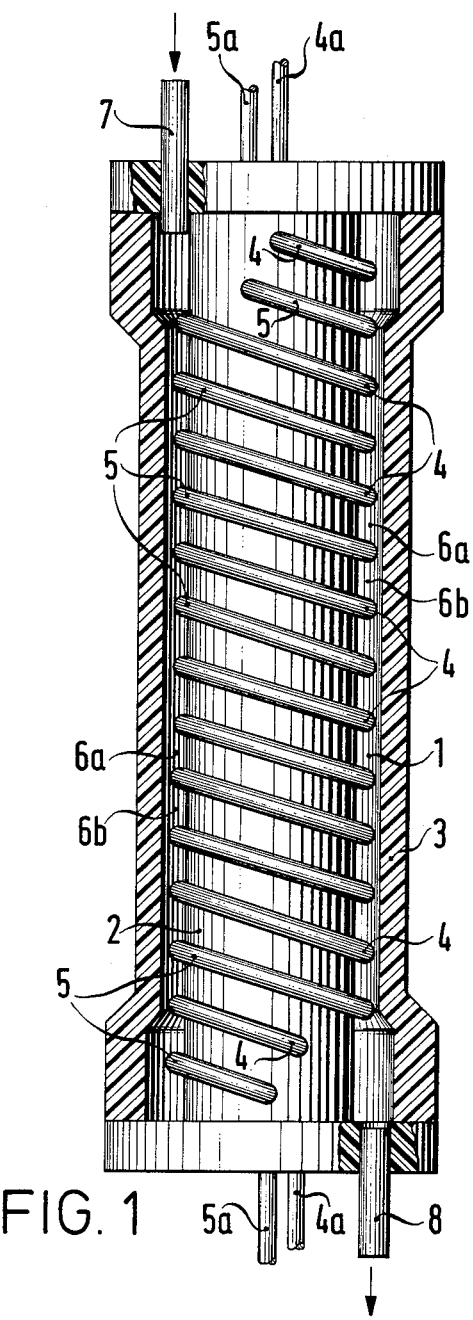
FIG. 1 is a longitudinal section through a chamber according to the present invention designed as a flow-through chamber with electrodes resting against the internal member in the form of a double helix.

As seen in FIG. 1, the space 1 of the chamber is bounded laterally by an internal member 2 and an outer cover 3 surrounding the internal member around its longitudinal axis. The internal member 2 is cylindrical, and the outer cover 3 is designed as a cylindrical jacket. Both members consist of polymethacrylate or a different plastic.

As also seen from FIG. 1, the electrodes 4 and 5, which consist of a winding of platinum wire, surround the internal member 2. The electrodes have the same separation from one another over their entire length. They are designed as loops in each case. The four electrode leads 4a, 4b, and 5a, 5b pass through the internal member 2 to the outside. The leads 4b and 5b can be connected to one another through a compensating resistor, which is not shown in the drawing.

The region bounded by the electrodes 4 and 5 in which the cells are exposed to the electrical field surrounds the internal member 2 as a component region 6a and 6b of the space 1, designed in the shape of a double helix.

The separation of the electrodes 4 and 5 from the inner wall of the outer cover 3 is constant over the entire length of the chamber, and in the example illustrated in the drawing, is approximately in the range from 100 $\mu$m to 500 $\mu$m.

The chamber illustrated in FIG. 1 is designed as a flow-through chamber and is closed at the faces. The inner surface of the outer cover 3 in FIG. 1 is a continuous surface to allow the suspension to flow unimpeded along the inner surface over a straight path. A sealable supply line 7 and a sealable discharge line 8 are provided for introducing the solution containing the cells.

Figure 2:
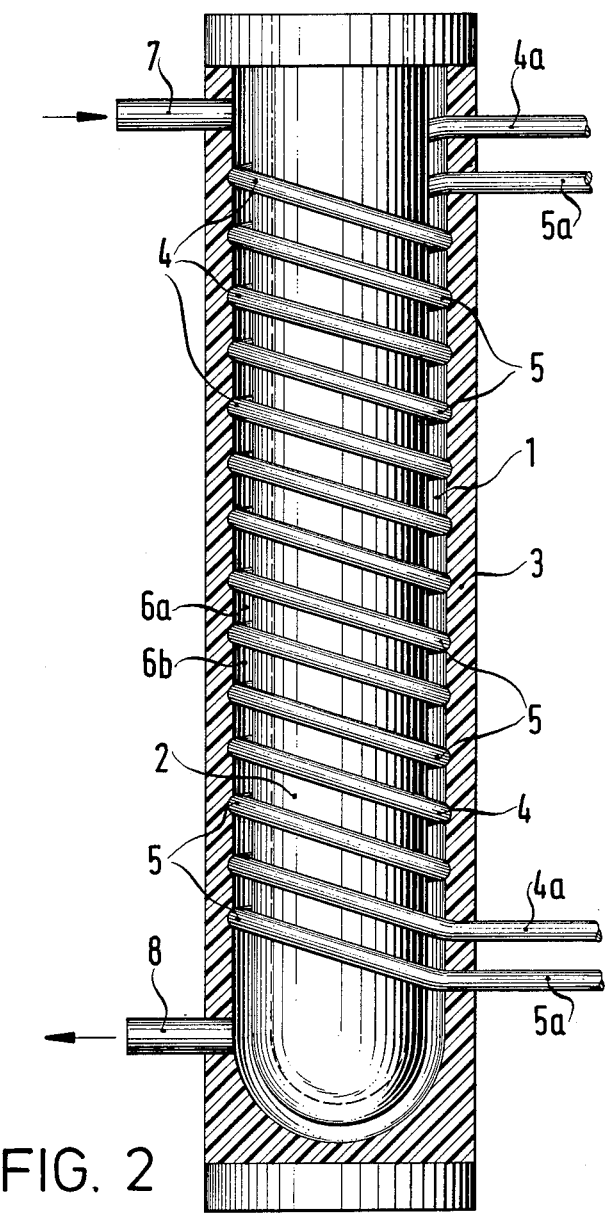
FIG. 2 is a longitudinal section through a chamber according to the present invention designed as a flow-through chamber with electrodes resting against the inner wall of the outer cover in the form of a double helix.

In the case of the chamber illustrated in FIG. 2, likewise designed as a flow-through chamber, in contrast to the form of embodiment of the chamber illustrated in FIG. 1, the electrodes 4 and 5 rest against the inner wall of the outer cover.

Figure 3:
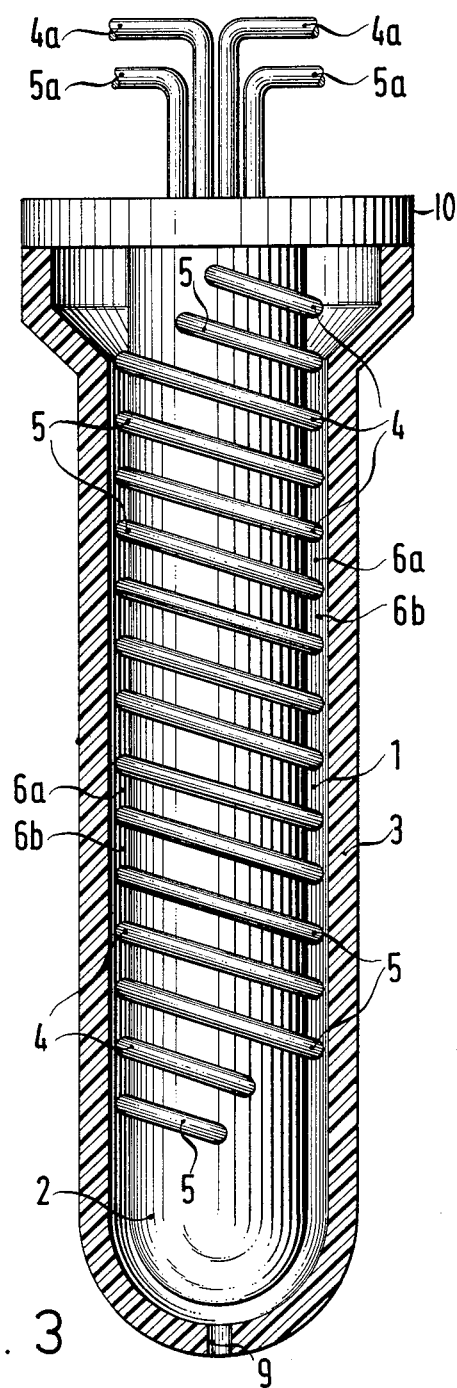
FIG. 3 is a longitudinal section through a chamber according to the present invention with an outer cover having the shape of a test tube and with internal member which can be inserted into the outer cover.

In the embodiment of the chamber illustrated in FIG. 3, the outer cover 3 has been designed to be sealed at one face, except for a sealable opening 9. The outer cover 3 has a cylindrical design, and except for the opening 9, has the form of a test tube. The internal member 2 is rod-shaped and is matched to the internal shape of the outer cover 3. The electrodes 4 and 5 rest against it, with their leads 4a, 4b, and 5a, 5b passing through the internal member to the outside. The region bounded by the electrodes, as in the embodiment of the chamber illustrated in FIG. 1, surrounds the internal member 2 as a component region 6a and 6b of the space 1 designed in the form of a double helix.

A seal 10 for the outer cover 3 is attached to the face of the internal member 2 corresponding to the open face of the outer cover 3.

Figure 4:
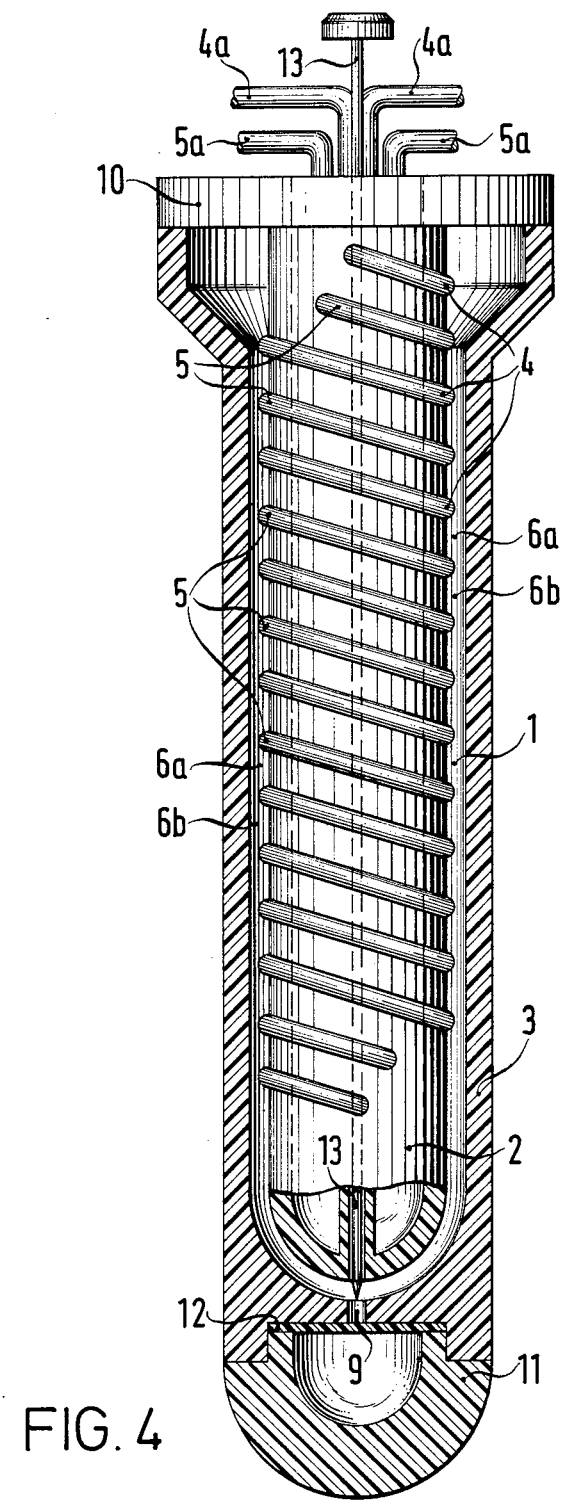
FIG. 4 is a longitudinal section through a chamber pursuant to FIG. 3, with accessory vessel which can be slipped onto the outer cover, and a guided movable needle in the internal member for puncturing the film of the accessory vessel.

The embodiment of the chamber illustrated in FIG. 4 starts from the embodiment illustrated in FIG. 3, but is supplemented by the accessory vessel 11. The outer cover 3 in the embodiment illustrated in FIG. 4 is so designed that the accessory vessel 11 can be slipped on. The opening 9 is not closed. The accessory vessel can be sealed by a film 12. It then serves to hold a liquid, such as a nutrient medium, which is not intended to reach the space 1 during the operation of the chamber. To puncture the film after the operation of the chamber, and in order to be able to centrifuge the cells in the space 1 into the accessory vessel, a movable needle 13 passing through the internal member 2 is provided.

Figure 5:
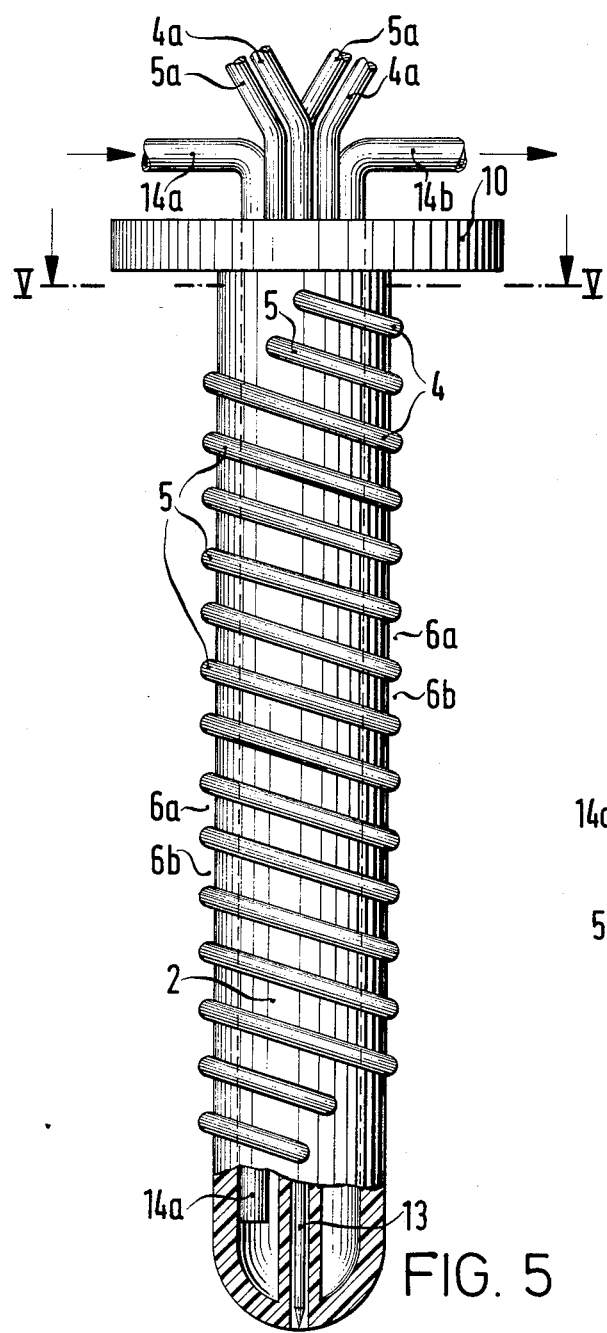
FIG. 5 is a longitudinal section through an internal member pursuant to FIG. 4 with a cooling line.

In FIG. 5, the internal member 2 pursuant to the form of embodiment of the chamber illustrated in FIG. 4 is shown, but with an added cooling system, through which a cooling medium can be conducted during the operation of the chamber. The cooling system consists of the feed line 14a, the cavity of the internal member into which the feed line 14a extends, and the discharge line 14b.

Figure 6:
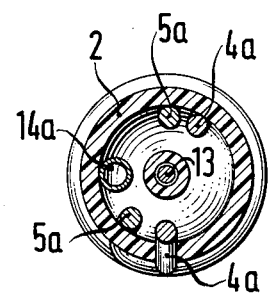
FIG. 6 is a cross-sectional view through the internal member of FIG. 5 taken along the Line A-B.

FIG. 6 shows a cross section through the internal member 2 of FIG. 5 along the Line V—V.

In all of the forms of embodiment of the chamber pursuant to the invention, the internal shape of the outer cover is matched to the shape of the internal member at a small distance of 20 μm to 500 μm if possible, but generally not less than 100 μm, so that the dead volume, or the volume in which cells are not exposed to the electrical field, is as small as possible. It is appropriate here for the distance between the electrodes and the wall opposite the electrodes, or the inner wall of the outer cover when the electrodes rest against the internal member, for example, to be of such a size that the suspended cells, and the fusion products in the case of a fusion of cells, are able to pass through the passageway between the electrodes and wall directly without damage.

When using devices to produce an alternating electrical field (for the formation of the sets of cells) with an output voltage of 50 $V_{p-p}$ at 50 Ω and a device to produce a square pulse (for the electrical breakdown) of 100 V at 50Ω, the distance of the electrodes from one another is generally 20 μm to 500 μm, depending on the type and size of the cells to be treated. It is approximately between 50 μm and 100 μm for yeast and bacterial cells, approximately between 100 μm and 200 μm for animal cells, and approximately between 100 μm and 500 μm for plant cells. The pitch of the multiple screw then results from the selected electrode separation. When using a device with higher output voltage and correspondingly higher power, the electrode separation can naturally be greater—for example 5 mm.

With larger electrode separation and thus also larger electrode cross section, it is beneficial for the electrodes to have a circular cross section. For example, this is the case when the electrodes consist of a wire wound on the internal member. Because of the circular cross section, an inhomogeneous field is developed between the electrodes, which is desirable with regard to the formation of a set of cells. It is appropriate here for the electrodes to be positioned recessed in their seats by approximately one-third of their diameter. In this way, the space for the cell suspension is kept as small as possible.

With very small electrode separations, at which the electrode screw cannot be wound of wire but other techniques must be used for the production of the electrode screw, an inhomogeneous electrical field is obtained when the electrodes rest as a flat strip against the internal member or the inner wall of the outer cover.

With an electrode length of more than approximately 1 m, the electrodes are suitably designed in each case as electrical loops, with each end of the electrodes being connected to an electrode lead. To avoid reflections in the electrode system, two corresponding leads of the electrodes, associated with one side of the multiple screw, are connected to one another through a resistor, with the resistor being balanced to the characteristic impedance. The other leads of the electrodes are then connected to the device or devices for the production of the electrical field.

As an example, with an outer cover and an internal member made of polymethacrylate and with platinum as electrode material, with an electrode separation of 200 μ and a frequency of the electrical voltage of 1 MHz and a conductivity of the suspension solution of approximately 0.5 to 1 mS, balancing of the resistance is not necessary when the electrodes do not exceed a length of 1.5 m.

In order to be able to observe the cells under a microscope during the operation of the chamber, it is suitable for the outer cover of the chamber to consist of transparent material such as polymethacrylate, and to have a flat design at at least one point on its outer jacket. The outer cover in this case can also have a hexagonal design, for example.

During the operation of the chamber, heating of the suspension containing the cells, which is undesirable for the cells, can occur as a result of the flow of current. This heating is counteracted in one embodiment of the chamber pursuant to the invention by passing a cooling line through the internal member. However, a cooling line can also be positioned in the outer cover.

As mentioned above, the chamber pursuant to the invention can be designed as a flow-through chamber, for example by positioning the supply and discharge lines on the faces of the chamber. To operate the chamber, a predetermined amount of cell suspension solution is then forced or drawn into the chamber, the electrical treatment is carried out, and the suspension solution in the chamber is then forced or drawn out of the chamber and replaced by a new quantity of cell suspension.

For flushing the chamber space with a cleaning solution after the electrical treatment of the cells, it can be appropriate for the internal member to have a system of pores opened toward the space of the chamber, accessible from the outside through a line, through which a liquid can be forced into the space, with the openings of the pores facing the space being smaller than the diameter of the cells to be treated. During the operation of the chamber, the pore system is then appropriately filled with the same solution in which the cells are suspended, but without cells.

However, the chamber of the embodiments of FIGS. 3 and 4 is constructed so-that the outer cover of the chamber is closed on one face, the internal member is rod-shaped and designed to match the internal shape of the outer cover, and a seal is provided for sealing the space at the open face of the outer cover. If the electrode leads do not pass through the space of the chamber, and the electrode leads are therefore fed to the outside through the internal member with the electrodes resting against the internal member, then the chamber can be loaded with cell suspension by introducing an amount of cell suspension into the outer cover, which appropriately has the shape of a test tube, which just fills the chamber space with the internal member immersed in the outer cover, and by distributing the liquid containing the cells throughout the entire space of the chamber by cautiously immersing the rod-shaped internal member.

It can also be suitable for the closed face of the outer cover to have an opening. If this can be sealed, then there is the possibility of proceeding initially as with the outer cover (which has no bottom opening) having the shape of a test tube, but of drawing off the cell suspension through the opening after carrying out the electrical treatment.

In the embodiment of the chamber of FIG. 4 an accessory vessel is removably connected with the opening in the outer cover. Appropriately, with the opening in the outer cover of the chamber closed, the electrical treatment of the cells is carried out first, and then the accessory vessel is fastened to the outer cover with the hole open, and the cells are then brought through the opening into the accessory vessel by centrifuging, with the chamber naturally being disconnected from the device or devices for producing the electrical field. The accessory vessel in this case can be filled with any arbitrary solution suitable for the further treatment of the cells, such as a nutrient or a selection medium.

In the embodiment of the chamber of FIG. 4, the accessory vessel is also fastened to the outer cover of the chamber during the electrical treatment. For this purpose, if there is a solution in the accessory vessel which should not reach the space of the chamber during the operation of the chamber, the connection between the space of the chamber and the inner space of the accessory vessel, leading through the opening in the outer cover, can suitably be shut off. This can be done, for example, by a shutoff element for the opening in the face of the outer cover which can be operated from the outside.

To close off the connection between the space of the chamber and the inner space of the accessory vessel leading through the opening in the face of the outer cover, the opening of the accessory vessel can also be covered over with a film 12. In this case, in order to bring the cells into the accessory vessel by centrifuging after their electrical treatment, a device operable from outside the chamber is provided, by means of which the film can be punctured when the accessory vessel is fastened to the outer cover.

Such a device can consist of providing a guided needle which can move in the internal member, by means of which the film can be punctured. However, such a needle can also be attached in the accessory vessel, and can specifically be operable from below.

The volume of the inner space of the accessory vessel is appropriately chosen so that the cell density of the cells centrifuged off into the accessory vessel after the electrical treatment is adequate for growth. In general, the volume, which depends on the size of the chamber, of course, is 500 l to approximately 2 ml.

As various changes could be made in the above constructions without departing from the scope of the invention, it should be understood that all matter contained in the above description or shown in the accompanying drawings shall be interpreted as illustrative and not in a limiting sense.

What is claimed is:

1. Chamber for the treatment of cells in an electrical field, comprising:
    a cylindrical internal member having non-conducting walls and an outer cover having non-conducting walls and a cylindrical inner surface which surrounds said internal member, said internal member's cylindrical outer surface having a shape matching said outer cover's cylindrical inner surface, said internal member and said outer cover having dimensions sufficient to form a space therebetween to hold a suspension containing the cells, said space being bound laterally by said internal member and said outer cover, said internal member and said outer cover having a common central longitudinal axis, said outer cover surrounding said internal member at a uniform distance from said central axis, said outer cover having an open end and a closed end, said open end being covered with a seal to enclose said space and said closed end having a second opening, said inner surface of said outer cover being a continuous surface to allow the suspension to flow unimpeded along said inner surface over a straight path from said open end to said closed end;
    at least two electrodes which extend into said space in such a way that a region bounded by said electrodes is formed between said electrodes, said electrodes developing an electrical field to which said cells are exposed, said electrodes extending into the space and surrounding the internal member by being wound around said internal member as a double helix with each of said wound electrodes having a constant pitch so that the region bounded by the electrodes forms a region in which the cells may be treated;
    an accessory vessel having an opening through which fused cells can pass, said vessel being removably connected to and contiguous with a bottom surface of the outer cover so that the opening of said vessel communicates with said second opening.

2. Chamber pursuant to claim 1 wherein the electrodes rest against the outer surface of said cylindrical internal member.

3. Chamber pursuant to claim 2 further comprising leads for said electrodes wherein said leads of said electrodes are fed through the internal member to the outer surface of said internal member.

4. Chamber pursuant to claim 1 wherein said electrodes rest against the cylindrical outer surface of said internal member and wherein the distance between the electrodes and the cylindrical inner surface of said outer cover is such that the suspended cells, and in the event of a fusion of cells, the fusion products, can pass through the passageway between the electrodes and said inner surface directly without damage.

5. Chamber pursuant to claim 1 wherein the distance between the electrodes is 20 $\mu$m to 500 $\mu$m.

6. Chamber pursuant to claim 1 wherein the electrodes have a circular cross section.

7. Chamber pursuant to claim 6 wherein the electrodes are positioned recessed into the cylindrical outer surface of said internal member against which said electrodes rest by approximately one-third of their diameter.

8. Chamber pursuant to claim 1 wherein said electrodes have a length of more than 1 m, and each of the electrodes is constructed as an electrical loop and each end of the electrodes is connected to an electrode lead.

9. Chamber pursuant to claim 1 wherein the outer cover consists of transparent material and has a flat surface at said open end.

10. Chamber pursuant to claim 1 wherein the internal member has a system of pores opened to the space of the chamber through which a liquid can be forced into the space, said system of pores being accessible from outside the chamber, the pores having openings facing the space which are smaller than the diameter of the cells to be treated.

11. Chamber pursuant to claim 1 further comprising means for sealing the opening of said accessory vessel wherein the connection between said second opening and the opening of the accessory vessel leading to said second opening in the face of the outer cover is sealed.

12. Chamber pursuant to claim 11 wherein said means for sealing comprises a film covering the opening of the accessory vessel.

13. Chamber pursuant to claim 12 further comprising a device operable from outside the chamber for puncturing the film.

14. Chamber pursuant to claim 1 further comprising a cooling line passing through said internal member to conduct a cooling medium during operation of the chamber.

* * * * *